United States Patent [19]

Kino et al.

[11] Patent Number: 4,742,007

[45] Date of Patent: May 3, 1988

[54] PROCESS FOR THE PREPARATION OF L-TRYPTOPHAN

[75] Inventors: Kuniki Kino; Toshihide Nakanishi; Masahiro Sugimoto, all of Yamaguchi, Japan

[73] Assignee: Kyowa Hakko Kogyo Kabushiki Kaisha, Japan

[21] Appl. No.: 702,560

[22] Filed: Feb. 15, 1985

[30] Foreign Application Priority Data

Feb. 22, 1984 [JP] Japan ................................ 59-32149

[51] Int. Cl.[4] .......................... C12P 13/22; C12N 1/20; C12R 1/15

[52] U.S. Cl. .................................... 435/108; 435/253; 435/843

[58] Field of Search .................... 435/108, 172.3, 193, 435/843, 253

[56] References Cited

U.S. PATENT DOCUMENTS 3,594,279  7/1971  Nakayama et al. .................. 435/108
4,535,060  8/1985  Comai ............................... 435/172.3

OTHER PUBLICATIONS

Metzler, Biochemistry, 1977, pp. 850–855.
Comai et al., "An AroA Gene Product Confers Resistance to the Herbicide Glyphosate", *Science*, vol. 221, (Jul. 22, 1983), pp. 370–371.
Rogers et al., "Amplification of the aroA Gene from *Escherichia coli* Results in Tolerance to the Herbicide Glyphosate", *Applied and Envir. Micro.*, vol. 46, No. 1, (Jul. 1983) pp. 37–43.
Japan, vol. 5, No. 164(C-76) (836), Oct. 21, 1981.
Japan, vol. 8, No. 236 (C-249) (1673), Oct. 30, 1984.

*Primary Examiner*—John E. Tarcza
*Attorney, Agent, or Firm*—Wolder, Gross & Yavner

[57] ABSTRACT

L-tryptophan can be prepared in good yield by a fermentation process which comprises culturing a novel L-tryptophan-producing microorganism of the genus *Corynebacterium*, which is resistant to at least one member selected from glyphosate [N-phosphonomethyl glycine], paraquat [1,1'-dimethyl-4,4'-bispyridinium] and derivatives thereof, and recovering L-tryptophan from the culture broth.

6 Claims, No Drawings

PROCESS FOR THE PREPARATION OF L-TRYPTOPHAN

FIELD OF THE INVENTION

The present invention relates to a fermentation process for the preparation of L-tryptophan.

DESCRIPTION OF THE PRIOR ART

It is known that L-tryptophan is useful, for example, as an additive for feedstuffs. Examples of known fermentation processes for the preparation of L-tryptophan include a process wherein a microorganism of the genus Corynebacterium, which is tyrosine and phenylalanine-requiring and resistant to tyrosine analogues and/or phenylalanine analogues is employed [Japanese Patent Kokai Koho No. 19037/76], a process wherein the microorganism employed is resistant to tryptophan analogues such as 5-methyltryptophan [ibid. Nos. 18828/83, 38795/76, 39517/78] and a process wherein a histidine-requiring microorganism is employed [ibid. No. 4505/82]. However, more advantageous processes for the preparation of L-tryptophan in good yield are desired.

The present invention is based upon the discovery that certain novel microorganisms of the genus Corynebacterium, which are resistant to N-phosphonomethyl glycine (hereinafter referred to as glyphosate) and derivatives thereof and/or to 1,1'-dimethyl-4,4'-bipyridinium (hereinafter referred to as paraquat) and derivatives thereof, are capable of producing increased amounts of L-tryptophan compared to the parent microorganisms without such resistance.

SUMMARY OF THE INVENTION

For the purpose of the present invention, any microorganism of the genus Corynebacterium, which is resistant to at least one member selected from glyphosate, paraquat and derivatives thereof may be used.

According to one aspect of the present invention, we therefore provide a process for the preparation of L-tryptophan which comprises culturing an L-tryptophan-producing microorganism of the genus Corynebacterium and recovering L-tryptophan from the culture broth, characterised in that said microorganism is resistant to at least one member selected from glyphosate, paraquat and derivatives thereof.

Preferred examples of novel microorganisms for use in a process according to the invention include Corynebacterium glutamicum H-3494 (phe$^-$, tyr$^-$, glyphosate-isopropylamine-resistant; hereinafter referred to as H-3494), Corynebacterium glutamicum H-3654 (phe$^-$, tyr$^-$, paraquat bismethylsulphate-resistant; hereinafter referred to as H-3654), Corynebacterium glutamicum H-3655 (phe$^-$, tyr$^-$, paraquat dichloride-resistant; hereinafter referred to as H-3655) and Corynebacterium glutamicum H-3656 (phe$^-$, tyr$^-$, PAP$^r$, PFP$^r$, tyrHx$^r$, pheHx$^r$, glyphosate-isopropylamine-resistant; hereinafter referred to as H-3656).

The significance of the abbreviations used above is as follows:
phe$^-$ = L-phenylalanine-requiring
tyr$^-$ = L-tyrosine-requiring
PAP$^r$ = p-aminophenylalanine-resistant
PFP$^r$ = p-fluorophenylalanine-resistant
tyrHx$^r$ = L-tyrosine hydroxamate-resistant
pheHx$^r$ = L-phenylalanine hydroxamate-resistant The above-mentioned microorganisms were deposited with The Fermentation Research Institute Agency of Industrial Science and Technology on 3rd Feb. 1984 as FERM-BP 674, FERM-BP 675, FERM-BP 676 and FERM-BP 677, respectively.

Glyphosate derivatives which may be used in the selection of microorganisms for use in a process according to the invention include salts with inorganic or organic bases, e.g. the sodium salt, the dimethylamine salt, the butylamine salt and the isopropylamine salt. Paraquat derivatives which may be used for the same purpose include salts with strong acids, e.g. the dichloride, the bromide, the iodide and the bismethylsulphate.

Mutant strains for use in a process according to the invention may be derived, for example, from Corynebacterium glutamicum ATCC 21854 (phe$^-$ and tyr$^-$; hereinafter referred to as ATCC 21854) by mutation in conventional manner, e.g. using ultraviolet rays or a known mutagen such as N-methyl-N'-nitro-N-nitrosoguanidine (hereinafter referred to as NTG) or nitrous acid. By way of illustration, the parent strain ATCC 21854 may be suspended in 0.05M phosphate-buffer solution (pH 7.0) and 250 μg/ml of NTG added to the suspension. The mixture is kept at 30° C. for 30 minutes to effect mutation. After this, the cells are collected, washed with 0.05M phosphate buffer solution and spread on an agar plate medium having the composition shown in Table 1 and in addition containing glyphosate-isopropylamine, paraquat dichloride or paraquat bismethylsulphate at sufficient concentration to inhibit the growth of the parent strain. After culturing at 30° C. for 3 to 10 days, colonies growing on the agar plate medium are separated and desired microorganisms capable of high productivity of L-tryptophan are selected.

The strains H-3494, H-3654 and H-3655 hereinbefore described were obtained using the above method. The mutant strain H-3656 was derived from Corynebacterium glutamicum ATCC 21851 (phe$^-$, tyr$^-$, PAP$^r$, PFP$^r$, tyrHx$^r$, pheHx$^r$; hereinafter referred to as ATCC 21851) in a similar manner.

TABLE 1

| Composition of minimal medium | | | | |
|---|---|---|---|---|
| Glucose | 20 g/l; | NH$_4$H$_2$PO$_4$ | | 1 g/l; |
| KCl | 0.2 g/l; | MgSO$_4$.7H$_2$O | | 0.2 g/l; |
| biotin | 30 μg/l; | L-tyrosine | | 10 mg/l; |
| L-phenylalanine | 10 mg/l; | | | |
| aqueous solution of trace amounts of metals | | | | 1 ml/l; |
| Na$_2$B$_4$O$_7$.10H$_2$O | 88 mg/l; | (NH$_4$)$_6$Mo$_7$O$_{24}$.4H$_2$O | | 37 mg/l; |
| MnCl$_2$.4H$_2$O | 72 mg/l; | FeCl$_3$.6H$_2$O | | 970 mg/l; |
| ZnSO$_4$.7H$_2$O | 8.8 mg/l; | CuSO$_4$.5H$_2$O | | 20 mg/l. |

[The pH is adjusted to pH 7.2].

Table 2 shows results which have been obtained on adding cells of the strain ATCC 21854, H-3494, H-3654, H-3655, ATCC 21851 or H-3656 to agar plate medium having the composition shown in Table 1 and, in addition, containing 50 μg/ml glyphosate isopropylamine, 800 μg/ml paraquat bismethylsulphate or 25 μg/ml paraquat dichloride. On each occasion, about 10$^6$ cells were added per plate (diameter 8.5 cm) and the number of colonies was determined after incubation for 4 days at 30° C.

TABLE 2

| | Number of colonies per plate | | | | | |
|---|---|---|---|---|---|---|
| Reagent (μg/ml) | ATCC 21854 | H-3494 | H-3654 | H-3655 | ATCC 21851 | H-3656 |
| No additive | ++ | ++ | ++ | ++ | ++ | ++ |
| glyphosate isopropyl | − | ++ | − | − | − | ++ |

TABLE 2-continued

| Reagent (μg/ml) | Number of colonies per plate | | | | | |
|---|---|---|---|---|---|---|
| | ATCC 21854 | H-3494 | H-3654 | H-3655 | ATCC 21851 | H-3656 |
| amine (50) paraquat bismethyl sulphate (800) | − | − | ++ | + | − | − |
| paraquat dichloride (25) | − | − | + | ++ | − | − |

Notes:
++ more than 500 colonies
+ not more than 100 colonies
− no colony

In a process according to the present invention, it is possible to use both synthetic and organic media containing suitable amounts of carbon sources, nitrogen sources and inorganic salts. Such media may, if desired, contain trace amounts of additional nutrients.

Preferred carbon sources include glucose, fructose, sucrose, maltose, mannose, sorbitol, starch, starch hydrolyzate, molasses and various other carbohydrates, sugar alcohols, glycerol, pyruvic acid, lactic acid, acetic acid, fumaric acid, gluconic acid and various other organic acids, ethanol and various other lower alcohols.

Preferred nitrogen sources include ammonia, ammonium chloride, ammonium sulphate, ammonium carbonate, ammonium acetate and various other inorganic and organic salts of ammonia, nitrogen-containing substances such as urea and various nitrogen-containing organic substances such as, for example, peptone, meat extract, yeast extract, corn steep liquor, casein hydrolyzate and soybean meal hydrolyzate.

Preferred inorganic salts include potassium phosphate, dipotasium phosphate, magnesium sulphate, sodium chloride, ferrous sulphate, manganese sulphate and calcium carbonate.

It is not always necessary to add, for example, vitamins, sources of amino acids and the like to the medium if such substances are present in other components.

Culturing of the microorganism may be effected aerobically, for example with shaking or agitation, preferably at a temperature from 20° to 40° C. and at a pH from 6 to 8 and desirably is continued for 2 to 5 days. After completion of culturing, L-tryptophan may be recovered from the culture broth by, for example, removing the cells from the culture broth by centrifugation and then concentrating the supernatant to crystallize the desired product or treating the supernatant with, for example, active carbon or ion exchange resin.

The following non-limiting examples illustrate the invention.

EXAMPLE 1

A seed medium [pH 7.2] having the composition of glucose (2%), polypeptone (1.5%), yeast extract (1.5%), sodium chloride (0.25%), urea (0.1%), L-tyrosine (200 μg/ml) and L-phenylalanine (200 μg/ml) was used to culture strain H-3494 at 30° C. for 24 hours. The resultant seed was transferred to a main medium (10 ml) in a 250 ml Erlenmeyer flask for culturing at 30° C. for 3 days with shaking to obtain 1.4 mg/ml of L-tryptophan. The composition of the main medium was as follows: glucose (6%); KH$_2$PO$_4$ (0.05%); MgSO$_4$.7H$_2$O (0.025%); ammonium sulphate (2%); biotin (30 μg/l); MnSO$_4$.7H$_2$O (10 mg/l); corn steep liquor (0.5%); CaCO$_3$ (2%) [pH 7.2].

After completion of culturing, the culture broth (2l) containing 1.4 mg/ml of L-tryptophan was centrifuged to remove the cells and calcium carbonate. The resultant supernatant was passed through a strongly acidic anion exchange resin (Diaion SK-104, H$^+$-form; commercial product of Mitsubishi Kasei Kogyo K.K., Japan) to adsorb L-tryptophan onto the resin, which was then washed with water. Elution of L-tryptophan was effected by the use of 0.5N aqueous ammonia and the eluant was concentrated to obtain crystals of crude L-tryptophan. The crystals were dissolved in a small amount of hot ethanol-water (50%). Following treatment with active carbon and finally decolorization and cooling, crystals of L-tryptophan were obtained (1.2 g).

EXAMPLE 2

Strains ATCC 21854, H-3654, H-3655, ATCC 21851 and H-3656 was treated in a similar manner to that described in Example 1 to obtain the results shown in the following Table 3.

TABLE 3

| Strains | Produced L-tryptophan (mg/ml) |
|---|---|
| ATCC 21854 | 0.2 |
| H-3654 | 1.0 |
| H-3655 | 0.9 |
| ATCC 21851 | 6.2 |
| H-3656 | 7.0 |

EXAMPLE 3

Strains ATCC 21854, H-3494, H-3654, H-3655, ATCC 21851 and H-3656 were cultured at 30° C. for 24 hours using the same medium as that described in Example 1. Each 1 ml of the culture broth was transferred to 10 ml of a main medium having the composition given below for culturing at 30° C. for 4 days with shaking. The results are shown in Table 4.

Composition of the main medium

Waste molasses (10%, calculated as glucose); KH$_2$PO$_4$ (0.05%); K$_2$HPO$_4$ (0.05%); MgSO$_4$.7H$_2$O (0.025%); ammonium sulphate (2%); corn steep liquor (1%); CaCO$_3$ (2%) [pH 7.2].

TABLE 4

| Strains | Produced L-tryptophan (mg/ml) |
|---|---|
| ATCC 21854 | 0.3 |
| H-3494 | 2.3 |
| H-3654 | 1.8 |
| H-3655 | 1.4 |
| ATCC 21851 | 11.5 |
| H-3656 | 12.8 |

EXAMPLE 4

Strains ATCC 21851 and H-3656 were cultured at 30° for 24 hours using a seed medium composed of waste molasses (7%, calculated as glucose); KH$_2$PO$_4$ (0.1%); K$_2$HPO$_4$ (0.1%), MgSO$_4$.7H$_2$O (0.05%), corn steep liquor (0.3%); and soybean meal hydrolyzate (0.9%, calculated as soybean meal; hydrolyzation was carried out with 6N H$_2$SO$_4$ and neutralization was subsequently carried out with aqueous ammonia). 300 ml of the culture broth was transferred to a 5 l jar fermenter containing 3 l of a main medium having the composition given below for culturing at 30° C. for 72 hours with shaking and aeration (3 l/min; 600 r.p.m.). The results are shown in the following Table 5.

Composition of the main medium

Waste molasses (15%; calculated as glucose); $KH_2PO_4$ (0.1%); $K_2HPO_4$ (0.1%); $MgSO_4.7H_2O$ (0.05%); corn steep liquor (0.1%); soybean meal hydrolyzate (0.9%, calculated as soybean meal) [pH 7.2].

TABLE 5

| Strains | Produced L-tryptophan (mg/ml) |
| --- | --- |
| ATCC 21851 | 16.8 |
| H-3656 | 18.2 |

What is claimed is:

1. A process for the preparation of L-tryptophan which comprises culturing an L-tryptophan-producing microorganism of the genus Corynebacterium and recovering L-tryptophan from the culture broth, characterized in that said microorganism is resistant to a member of the group consisting of paraquat and derivatives thereof.

2. The process of claim 1 wherein said microorganism is a strain of *Corynebacterium glutamicum*.

3. The process of claim 2 wherein said microorganism is selected from the group consisting of *Corynebacterium glutamicum* H-3654 (FERM BP 675) and *Corynebacterium glutamicum* H-3655 (FERM BP 676).

4. The process of claim 1 wherein culturing is effected under aerobic conditions at a temperature of 20° C. to 40° C. and a pH of from 6 to 8 for 2 to 5 days.

5. A biologically pure culture of the microorganism *Corynebacterium glutamicum* H-3654 (FERM BP 675) or mutant strain thereof capable of producing L-tryptophan when cultured.

6. A biologically pure culture of the microorganism *Corynebacterium glutamicum* H-3655 (FERM BP 676) or a mutant strain thereof capable of producing L-tryptophan when cultured.

* * * * *